(12) United States Patent
Quist et al.

(10) Patent No.: US 6,972,424 B1
(45) Date of Patent: Dec. 6, 2005

(54) HIGH DETECTION RATE PARTICLE IDENTIFIER

(75) Inventors: Gregory M. Quist, Escondido, CA (US); Donald C. Mead, Carlsbad, CA (US); Hanno Ix, Escondido, CA (US)

(73) Assignee: PointSource Technologies, LLC, Solana Beach, CA (US)

( * ) Notice: Subject to any disclaimer, the term of this patent is extended or adjusted under 35 U.S.C. 154(b) by 385 days.

(21) Appl. No.: 10/412,100

(22) Filed: Apr. 11, 2003

Related U.S. Application Data

(60) Provisional application No. 60/373,221, filed on Apr. 16, 2002.

(51) Int. Cl.$^7$ .............................................. G01N 15/06
(52) U.S. Cl. .................... 250/573; 250/222.2
(58) Field of Search ................ 250/573, 574, 250/575, 222.2; 356/337, 338

(56) References Cited

U.S. PATENT DOCUMENTS

| | | | |
|---|---|---|---|
| 3,770,351 A | 11/1973 | Wyatt | |
| 3,901,602 A | 8/1975 | Gravatt et al. | |
| 4,070,113 A | 1/1978 | Frazer et al. | |
| 4,173,415 A | 11/1979 | Wyatt | |
| 4,265,538 A | 5/1981 | Wertheimer | |
| 4,548,500 A | 10/1985 | Wyatt et al. | |
| 4,565,448 A | 1/1986 | Abbott et al. | |
| 4,639,137 A * | 1/1987 | Hazan et al. | ............... 356/339 |
| 4,702,598 A | 10/1987 | Böhmer | |
| 4,728,190 A | 3/1988 | Knollenberg | |
| 4,906,094 A | 3/1990 | Ashida | |
| 4,907,884 A | 3/1990 | Stevens et al. | |
| 4,942,305 A | 7/1990 | Sommer | |
| 4,952,055 A | 8/1990 | Wyatt | |
| 4,987,539 A | 1/1991 | Moore et al. | |
| 5,125,737 A | 6/1992 | Rodriguez et al. | |
| 5,247,340 A | 9/1993 | Ogino | |
| 5,305,071 A | 4/1994 | Wyatt | |

(Continued)

FOREIGN PATENT DOCUMENTS

GB      2317228 A      3/1998

OTHER PUBLICATIONS

"Recent Overview Article—Aerosol Characterization Research at the University of Hertfordshire", by Prof. Paul Kaye, STRC Particle Instruments Research Group, Science and Technology Research Centre, University of Hertfordshire, Hatfield, United Kingdom, reproduced from the Aerosol Society Newsletter, No. 33, Sep. 18-20, 1998.

(Continued)

*Primary Examiner*—Que T. Le
(74) *Attorney, Agent, or Firm*—Leon D. Rosen

(57) ABSTRACT

An improvement is described for use in a system that identifies particles in a fluid such as water by passing the fluid through a passage in a transparent carrier and detecting light from a laser beam that is scattered by particles, followed by comparing the scatter pattern to those of known particles, which increases the rate at which particles are detected. A plurality of transparent carriers with through passages are provided, and a narrow beam is directed through each carrier to scatter light from particles at a detect zone in each carrier passage. In one arrangement (60), the carriers (62, 64, 66) are connected in series, so a limited amount of water passes through detect zones (24A, 24B. 24C) to generate a high rate of particle detection. In another arrangement (130), the carrier passages are connected in parallel, so when a larger sample of water is available different parts of the water sample pass through different carrier passages, to again increase the rate of particle detection.

10 Claims, 3 Drawing Sheets

U.S. PATENT DOCUMENTS

| | | |
|---|---|---|
| 5,414,508 A | 5/1995 | Takahashi et al. |
| 5,436,465 A | 7/1995 | Borden et al. |
| 5,534,999 A | 7/1996 | Koshizuka et al. |
| 5,627,040 A | 5/1997 | Bierre et al. |
| 5,737,078 A | 4/1998 | Takarada et al. |
| 5,999,256 A | 12/1999 | Jones et al. |
| 6,023,324 A | 2/2000 | Myers |
| 6,100,541 A | 8/2000 | Nagle et al. |
| 6,118,531 A | 9/2000 | Hertel et al. |
| 6,120,734 A | 9/2000 | Lackie |
| 6,313,908 B1 | 11/2001 | McGill et al. |
| 6,421,121 B1 | 7/2002 | Haavig et al. |

OTHER PUBLICATIONS

"Discrimination of phytoplankton via light-scattering properties", by Philip J. Wyatt and Christian Jackson, Limnology And Oceanography, 34(1), 1989, pp. 96-112, American Society of Limnology and Oceanography, Inc.

* cited by examiner

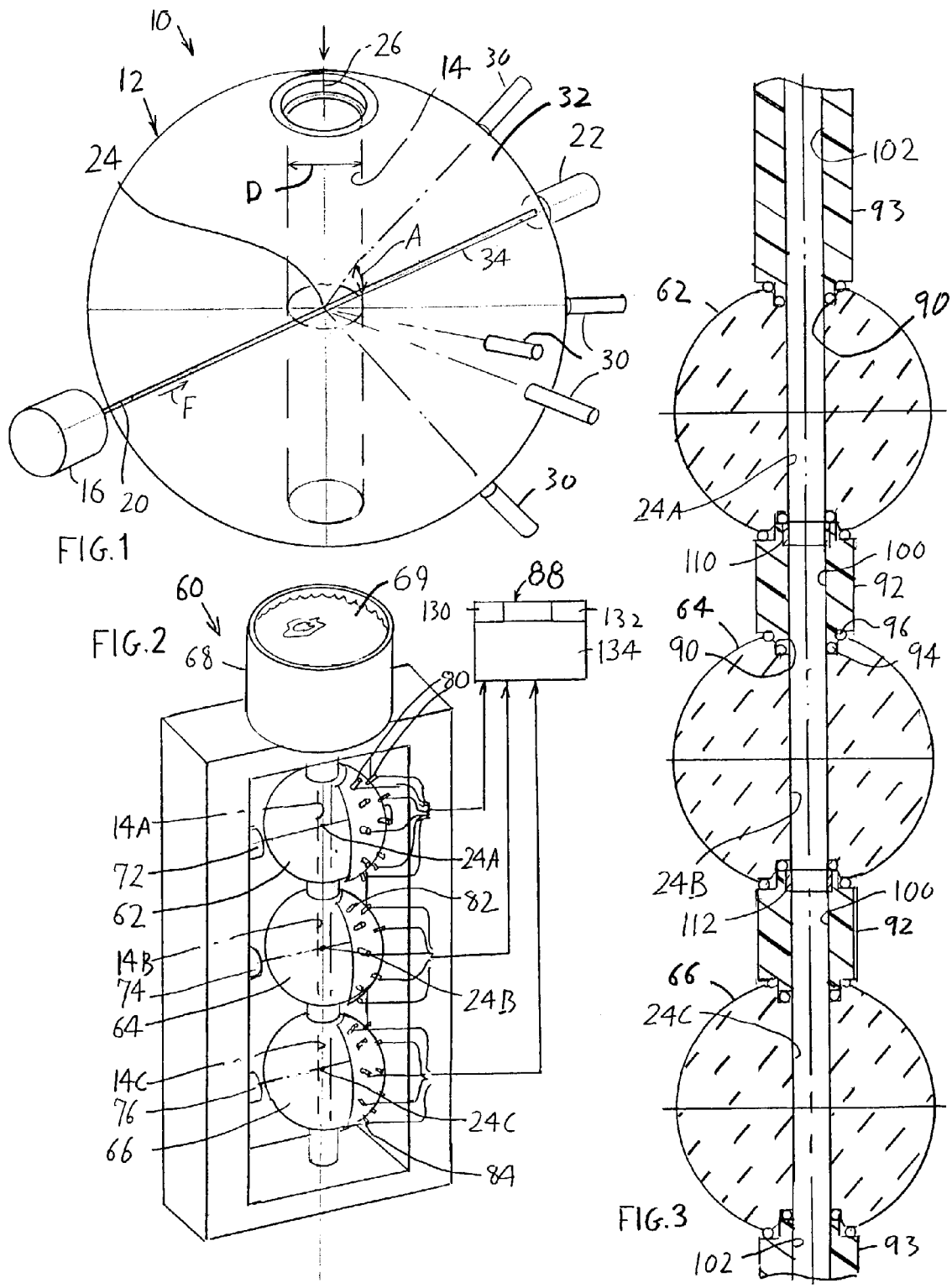

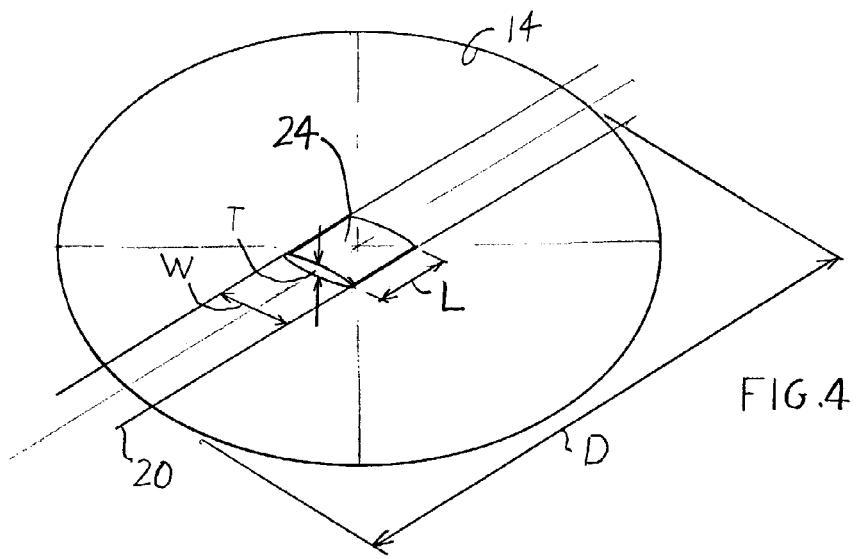
FIG. 4
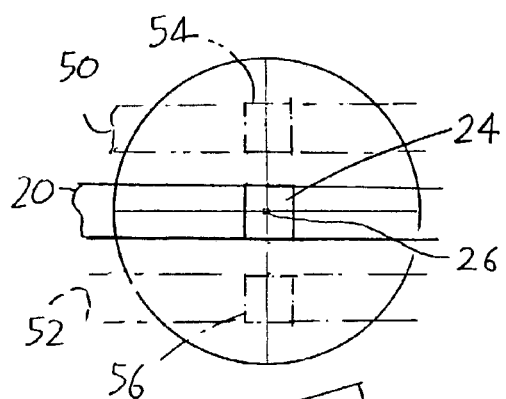
FIG. 5
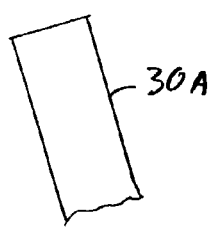
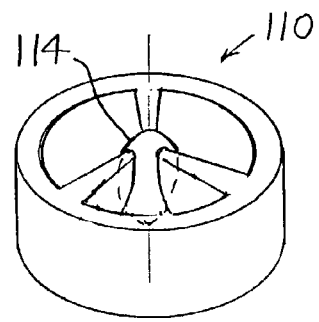
FIG. 6

US 6,972,424 B1

HIGH DETECTION RATE PARTICLE IDENTIFIER

CROSS-REFERENCE

Applicant claims priority from U.S. provisional application Ser. No. 60/373,221 filed Apr. 16, 2002.

BACKGROUND OF THE INVENTION

There is a need to detect and/or identify unknown microscopic particles (e.g. up to about 50 microns diameter) such as pathogenic microorganisms in fluid such as water or air. Applicant's earlier U.S. Pat. No. 6,519,033 describes a system for detecting and identifying such particles. A laser beam is directed through the water, with a small region of the water being designated to be a detect zone. Photodetectors are aimed precisely at the detect zone. When a particle passes through the detect zone, it scatters laser light, and the scattered light is detected by the photodetectors. This can be referred to as an interrogation of the particle. The outputs of the photodetectors are delivered to a computer which compares the light scatter pattern (eventvector) of the particle to light scatter patterns of particles of each of a plurality of known species of particles, such as species of pathogens. The computer can indicate whether the unknown particle that was just detected, is of one of the plurality of species of particles whose scatter patterns are recorded in the computer's memory.

Since the filing date of the above application, applicant has developed carriers each consisting of a glass sphere with a passage bored through it. Water to be tested is flowed through the passage. In one example, the passage has a diameter of 9 mm and the detect zone from which scattered light is detected has a width and length of 1.5 mm and a thickness of 0.1 mm. Water at a velocity such as 8 cm per second can be flowed in laminar flow through the passage. With such a velocity, it takes 1.5 milliseconds for a particle to move through the beam of a thickness of 0.1 mm. If one assumes that the liquid contains 500 particles per milliliter, the fluid passes at a velocity of 8 cm per second, and the detect zone has the above-described dimensions, one would expect about 100 particles per second to pass through the detect zone. Each particle takes about 1.5 milliseconds to pass through the beam. If the water has very few particles, such as five particles per milliliter, then one might expect to detect only one particle per second.

A large number of particles such as thousands, typically must be interrogated in order to determine the condition of the water. Many particles will be algae of different known species. Occasionally, a particle may be one of the pathogens that passes through a water treatment plant, and is one of the known species programmed into the computer. A danger generally does not arise from a few pathogens, but only from a considerable density of pathogens in the water. A large number of particles may have to be interrogated to determine the density of particles in the water, so as to determine whether the water is acceptable or not. If the apparatus detects only about one particle per second, then it may take a few thousand seconds to detect a few thousand particles so as to obtain a reliable reading on the quality of the water. It may take an hour to interrogate a few thousand particles, and such a period of time may be unacceptable for several reasons, including where a researcher has to wait around for the data, or where the delay can result in considerable quantities of unhealthy water being pumped through a municipal water system before the problem is caught. Apparatus that increases the rate of particle detection would be of value.

SUMMARY OF THE INVENTION

In accordance with one embodiment of the present invention, a system is provided for detecting and/or identifying particles in a fluid such as water, which enables the more rapid detection of particles. The system includes a plurality of carriers that each comprises transparent material through which a light beam passes and which has a passage through which fluid can flow, so a particle passing through a detect zone lying along the light beam can produce light scatter patterns. To increase the rate at which particles are detected, applicant provides a plurality of carriers, and a source for a plurality of light beams that each passes through one of the carriers to produce a scatter pattern that is detected and analyzed. The plurality of carriers can be connected in series or in parallel. A connection in series enables the detection of a high percent of particles in a water sample that has a limited sample volume. A connection in parallel is especially useful where there is plenty of water available to be interrogated.

The novel features of the invention are set forth with particularity in the appended claims. The invention will be best understood from the following description when read in conjunction with the accompanying drawings.

BRIEF DESCRIPTION OF THE DRAWINGS

FIG. 1 is an isometric view of a portion of a particle identifying system of the present invention, showing a transparent carrier, a laser light source, and photodetectors.

FIG. 2 is an isometric view of a system of the invention, wherein a plurality of carriers of the type illustrated in FIG. 1, are connected in series, and each has a light source and photodetectors.

FIG. 3 is a sectional side view of only the carriers and conduits that connect them in series, of FIG. 2.

FIG. 4 is an isometric representation of the detect zone and passage of the carrier of FIG. 1.

FIG. 5 is a plan view of the detect zone and passage of FIG. 4, showing one possibility for increasing detection rate, which is fraught with problems.

FIG. 6 is an isometric view of a fluid distributer of a type that can lie between carriers in FIG. 3.

DESCRIPTION OF THE PREFERRED EMBODIMENTS

Figure 3A:
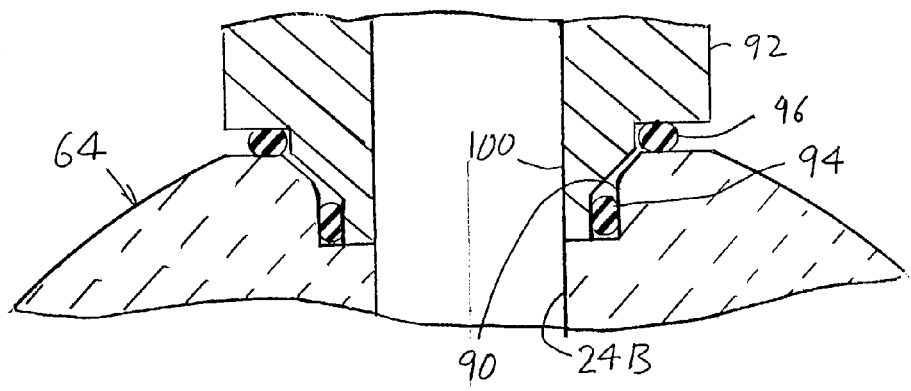
FIG. 3A is an enlarged sectional view of an end portion of one of the carriers of FIG. 3.

FIG. 1 illustrates part of a particle identifying system 10 which includes a carrier element or carrier 12 with a passage 14. Fluid such as water containing microscopic particles to be detected, flows through the passage. A light source in the form of a laser 16 generates a laser light beam 20 that passes through the carrier 12, with most of the laser beam energy absorbed by a dump 22. The laser beam extends primarily perpendicular to the passage, and preferably extends perpendicular to the passage. In one example, the laser beam is red light of a wavelength of 0.6 microns, and is used to detect particles having a diameter on the order of three microns (0.3 to 30 microns).

The laser beam 20 passes through a detect zone 24 lying along the axis 26 of the passage. When a particle in the fluid passes through the detect zone, the particle scatters light in multiple directions. A plurality of photodetectors 30 spaced around the carrier, detect light scattered in multiple directions. The intensity of light scattered in each of multiple directions is a pattern that can be used to identify the species of the unknown particle that has just passed through the detect zone 24. This is accomplished by comparing light scattered in the different directions by an unknown particle, to light scattered by particles of known species when they were passed through the system. U.S. Pat. No. 6,519,033 describes a method for comparing the scatter patterns.

It is noted that in some cases it is desired to determine only the presence of a particle. For example, there may be a need to determine the density of microscopic particles (e.g. from 0.3 to 30 microns) in a fluid. In that case, only a single photodetector may be required.

In FIG. 1, the laser beam 20 is assumed to move in a forward F direction. The carrier is formed of glass having an index of refraction of 1.55. If the carrier has cylindrical outer walls, then light scattered from the detect zone 24 at an angle A of up to 410 above or below the laser beam path 34 would pass through the interface of the glass and surrounding air and reach the photodetectors 30. However, if the scatter angle A above or below the beam path 34 is more than 410, then such light would be internally reflected by a cylindrical surface. To avoid this, applicant constructs the front of the carrier 12 with a spherical outer surface 32 having a sphere center lying in the carrier passage (or constructs the carrier front surface with conical upper and lower surfaces).

In one example, the passage has a diameter D of 9 mm and the carrier has a spherical outside diameter of 64 mm. As indicated in FIG. 4, the laser beam at the detect zone 24, has a width W of 1.5 mm and a thickness T of 0.1 mm. The detect zone has a width W of 1.5 mm and a length L of 1.5 mm. If the concentration of microscopic particles in the fluid is 500 particles per $cm^3$ and the fluid is moving downward at a velocity of 8 cm per second, then one might expect to have a particle pass through the detect zone at an average of once per 10 milliseconds. We might expect there to be two particles passing simultaneously through the detect zone 24 once in every ten particle detections. The detection of two particles simultaneously in the detect zone is not used by applicant, so such detections are useless and are preferably scarce. The small thickness T of the laser beam is desirable to minimize the number of occurrences of two particles lying simultaneously in the detect zone.

FIG. 5 shows that the area occupied by the detect zone 24, as viewed along the axis 26 of the passage, is about 2.25 $mm^2$. With a passage diameter D of 9 mm, and a passage area of 64 $mm^2$, the detect zone 24 occupies only about 3.5% of the cross-sectional area of the passage. As a result, about 96.5% of the particles in the fluid are not detected. For accurate identification of pathogens in a fluid that may contain primarily other microscopic particles, it is desirable that a very large number of detections take place for a sample of given volume, and during a moderate period of time of perhaps one minute. It might be thought that the diameter D of the passage could be reduced to slightly over 1.5 mm and the fluid could be moved rapidly through the passage. However, as the diameter of the passage decreases, capillary effects occur, where surface tension of the fluid resists rapid fluid movement, and where rapid fluid movement can result in turbulence and consequent generation of microscopic bubbles. Microscopic bubbles reflect original laser light and scattered light, and can prevent accurate operation of the system.

It would be possible to direct a few laser beams such as 50 and 52 in FIG. 5, in addition to the original laser beam 20. Then, it would be possible to provide additional groups of photodetectors that are each directed at a corresponding one of the detect zones such as 54, 56, in addition to the original detect zone 24 lying along laser beam 20. This has the disadvantage that a photodetector 30A oriented at certain angles and directed at one detect zone 24, might pick up light from another detect zone. Also, there is a greater possibility of a photodetector picking up light reflected from walls of the passage.

In accordance with one embodiment of the present invention, applicant provides a system 60 shown in FIG. 2, which includes a plurality of carriers 62, 64, 66 with passages 14A, 14B, 14C. The passages are all connected to the same fluid source 68 so fluid 69 from the source can flow simultaneously through all of the carriers 62–66. In FIG. 2, the carriers are connected in series, so the same fluid that passes through a passage 14A of the first carrier 62, subsequently passes through passages 14B, 14C of the other carriers. Three corresponding lasers 72, 74, 76 direct separate light beams through each of the carriers, and through corresponding detect zones 24A, 24B and 24C. (A single laser beam can be split into three beams). Three sets of photodetectors 80, 82, 84 are connected to a computer 88 which compares the pattern of light scatter from each of the detect zones 24A, 24B, 24C to patterns previously recorded for known species of particles, such as pathogenic bacteria. The computer 88 has a memory 130 which stores numerous scatter patterns for particles that are all of one species, such as thousands of scatter patterns for particles of a particular species that were positioned in different orientations when they passed through the detect zone, and that vary somewhat in shape and size. The memory preferably holds multiple scatter patterns for each of several species. The memory also stores the scatter pattern for the unknown particle. A comparer 132 which is a stored program that directs a central processing unit 134 to make computations, compares the pattern of the unknown particle to the patterns for the known species of particles to look for a match.

There is a slight possibility that a particle detected at one detect zone such as 24A, would be detected at one of the other detect zones 24B or 24C. However, the possibility is low, such as about 7% in the above example for the size of the detect zone and the diameter of the passage when three carriers are used. However, even if such double detection of a particle occurs, it can be useful because it is not only the species of the particle, but the particular orientation of the particle that is detected and that is used to determine whether the particle is one of a known group of species of particles.

FIG. 3 shows the manner in which the carriers 62–66 are connected in series, with FIG. 3A showing greater details. Each carrier has a recess 90 at each of its ends. A coupling 92, 93 projects into the recess and has surfaces that press against O-rings 94, 96. The passage 100, 102 in each coupling is of the same size as the passage such as 24B in the carrier 64, and they are aligned, to avoid turbulence and consequent generation of microscopic bubbles. A fluid distributer 110, 112 is shown lying between pairs of carriers to move full with lying at the middle of one carrier passage toward the periphery of a next passage. One example of such distributer is shown in FIG. 6, in which an aerodynamically-shaped part 114 diverts fluid away from the middle of the passage, while minimizing turbulence.

In FIG. 2, a large container forms the source 68 that holds a fluid 69 such as water that has just been taken from a reservoir at a water treatment plant. The water flows through the carriers by gravity, with tests indicating a flow rate of about 8 cm per second for a single carrier of the type described above.

Figure 7:
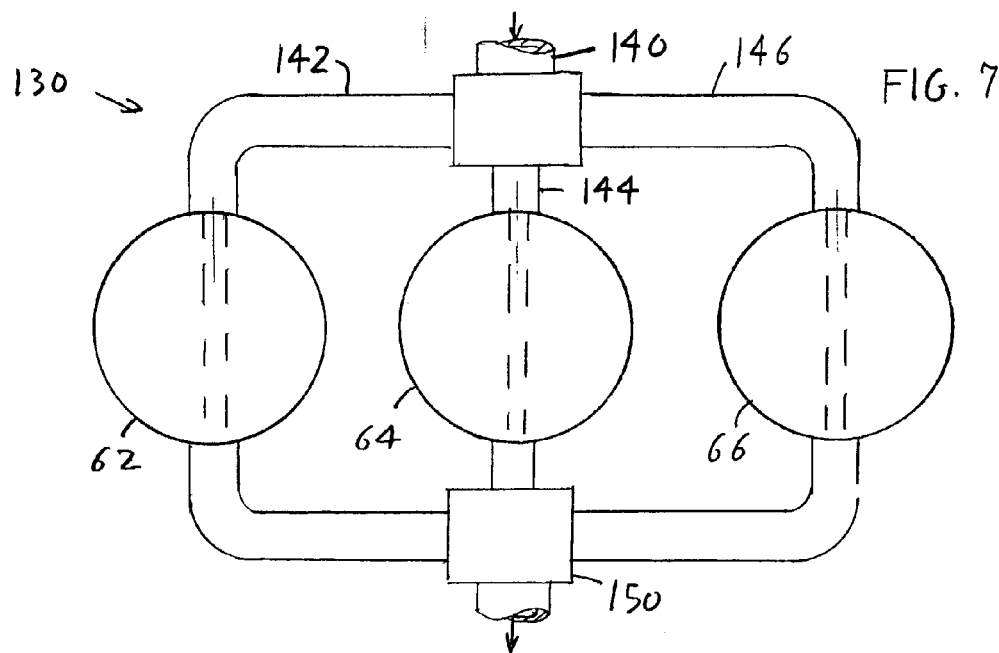
FIG. 7 is a sectional view of a group of carriers of the type illustrated in FIG. 1, but connected in parallel.

FIG. 7 illustrates another system 130 in which the carriers 62, 64, 66 are connected in parallel rather than in series. This is especially useful where the size of the sample is virtually unlimited, as where some water in a reservoir of a water treatment plant is pumped through a pipe 140 to couplings 142, 144, 146. The couplings connect to the passages of the carriers. The outputs of the carriers are delivered through a coupling 150 back to the reservoir. A connection in series has the advantage that no particle will pass through two or three detect zones and produce a plurality of scatter patterns to be analyzed. However, the parallel connection of FIG. 7 requires a greater through flow of water than a series connected system. A valve can be positioned along each conduit 142–146, so all but one of the valves can be closed, if the sample volume is limited.

Figure 8:
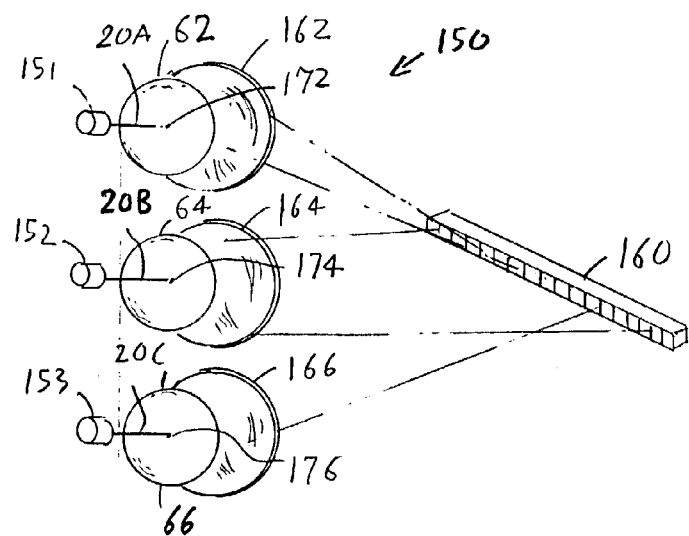
FIG. 8 is an isometric view of a group of carriers similar to that of FIG. 2, but with a different detection arrangement.

FIG. 8 illustrates another system 150 which includes the three carriers 62, 64, 66 connected in parallel or in series. A light source comprising three lasers 151–153 produce laser beams 20A, 20B, 20C that pass through a detect zone in each carrier, and the scattered light must be detected by photodetectors. However, instead of using three separate sets of photodetectors, applicant uses a single row 160 of CCD's (charge coupled detectors). Also, applicant uses three plate-shaped holograms 162, 164, 166. Each hologram directs light scattered from each corresponding detect zone 172, 174, 176 to corresponding CCD photodetectors of the row 160. If there are a large number of particles per volume of water, so there is often an occurrence where two particles (in one or more detect zones) are detected simultaneously, then the laser beams can be derived from three different lasers that are each operated to generate short duration (e.g. 300 microseconds) pulses in sequence. Otherwise, a single laser beam can be broken up into the three beams 20A, 20B, 20C.

Thus, the invention provides a system for detecting and/or identifying particles in a fluid, by detecting scattering of light as a particle passes through a detect zone of a carrier, which increases the detection rate of particles. A plurality of carriers are provided, that are connected so at least portions of the sample fluid such as water passes through all of the carriers. The carriers can be connected in series, or in parallel, and when a large number of carriers are used they can be connected in both series and parallel. Conduits that connect to carriers, can have the same internal cross-section as the carrier passages, such as the same diameter for cylindrical passages in the carrier and conduit, with the end of each passage being enlarged to receive a conduit end and an O-ring.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A system for detecting and/or identifying particles in a fluid, which includes a light-transmitting carrier element having a passage through which said fluid can pass, a light source that directs a light beam through said passage, and at least one photo detector that detects light scattered from a detect zone region that lies along said light beam and in said passage, comprising:
   a plurality of carriers, including said carrier element, that each have a passage through which fluid can flow;
   said light source is constructed to direct a light beam through the passage of each of said carriers;
   said at least one detector is constructed to detect light scattered from each of a plurality of detect zones, including said detect zone region; and
   a plurality of conduits connected to the passages of said carriers, which directs portions of said fluid through each of said passages.

2. The system described in claim 1 wherein:
   said plurality of conduits connect the passages of said plurality of carrier in series, whereby to detect more particles in a given amount of fluid.

3. The system described in claim 2 including:
   means in one of said conduits which connects two of said passages in series, for directing some of the fluid lying at a periphery of the one conduit, toward the middle of the one conduit.

4. The system described in claim 1 wherein:
   said plurality of conduits connect the passages of said plurality of carriers in parallel, whereby to avoid detecting the same particles twice.

5. The system described in claim 1 wherein:
   each of said carriers is formed of a rigid transparent material, each of said passages has a uniform first width along most of its length and has opposite carrier ends where the passage width is increased, and one of said conduits has a conduit end that lies in said passage and that has an inside width equal to said first width, and including an O-ring elastomeric seal that seals an outside surface of said conduit end to an inside surface of one of one of said passage ends.

6. The system described in claim 1 wherein:
   said at least one detector comprises a plurality of sets of detectors, each set of detectors positioned to detect light scattered from only one of said detect zones.

7. A system for detecting and/or identifying particles in a quantity of a fluid from a fluid source, comprising:
   a plurality of carriers, each having a forward outer surface and each having a through carrier passage;
   means for directing a plurality of light beams in a forward direction through each of said carriers, with each light beam passing through the passage of the carrier, each carrier passage extending primarily perpendicular to the light beam;
   a plurality of photodetectors that each detects light scattered from a detect zone that lies in one of said carrier passages and that also lies along the corresponding light beam;
   a plurality of conduits that connect said fluid source to each of said carrier passages to flow said fluid through all of said passages.

8. The system described in claim 7 wherein:
   said plurality of conduits connects said carrier passages in series, so the same fluid passes through each of a plurality of carrier passages.

9. The system described in claim 7 wherein:
   said plurality of conduits connects said carrier passages in parallel, so different portions of said quantity of fluid pass through different ones of said carrier passages but not others.

10. The system described in claim 7 including:
    a computer that has a memory that stores the outputs of the photodetectors that detect light scattered from said detect zones, and that has a program that analyzes the outputs of said photodetectors to indicate whether the outputs of photodetectors that all detect light scattered from a particle lying in one of said detect zones, indicates that said particle is of one of a group of known particle species;
    said photodetectors that detect light scattered from each of said detect zones, are all connected to said computer.

* * * * *